United States Patent [19]

Clement

[11] Patent Number: 4,766,908
[45] Date of Patent: Aug. 30, 1988

[54] ASPIRATION SYRINGE

[75] Inventor: Thomas P. Clement, Bloomington, Ind.

[73] Assignee: Van-Tec, Inc., Spencer, Ind.

[21] Appl. No.: 2,037

[22] Filed: Jan. 12, 1987

[51] Int. Cl.⁴ .................................................. A61B 5/00
[52] U.S. Cl. .................................... 128/765; 128/770; 604/187; 604/221
[58] Field of Search ........................ 128/760, 763–766, 128/770; 604/51, 52, 118, 121, 187, 207, 208, 221, 230, 264, 272

[56] References Cited

U.S. PATENT DOCUMENTS

| 577,682 | 2/1897 | Eissner . | |
|---|---|---|---|
| 686,332 | 11/1901 | Prescott . | |
| 840,472 | 1/1907 | Brookes . | |
| 1,343,085 | 6/1920 | Lerch . | |
| 1,898,435 | 2/1933 | Fillauer . | |
| 2,672,866 | 3/1954 | Kater | 604/207 |
| 3,660,037 | 5/1972 | Sokol | 128/765 |
| 3,699,961 | 10/1972 | Szpur . | |
| 3,828,778 | 8/1974 | Weinhart . | |
| 3,985,122 | 10/1976 | Topham | 128/765 |
| 4,030,498 | 6/1977 | Tompkins | 604/221 |
| 4,245,654 | 1/1981 | Raitto . | |
| 4,361,155 | 11/1982 | Anastasio . | |
| 4,469,482 | 9/1984 | Lissenburg et al. | 604/187 |
| 4,515,591 | 5/1985 | Hemmerich et al. . | |

Primary Examiner—Max Hindenburg

[57] ABSTRACT

An aspiration syringe suitable for one-handed operation has a barrel defining a bore, a plunger consisting of a small cross-section plunger shaft extending into the bore and a first seal within the bore, carried by the distal end of the shaft for axial movement within the bore, and an end closure across the bore proximal of the first seal, the plunger shaft extending in sliding, sealed engagement therethrough. The first seal engages the wall defining the bore in vacuum-tight sealing engagement. The transverse cross-sectional area of the shaft is much less than the transverse cross-sectional area of the bore to provide a syringe-actuating vacuum chamber of substantial volume within the bore between the seal and the end closure. Movement of the plunger shaft to carry the first seal distally, from a first position, away from the end closure, creates a vacuum condition within the vacuum chamber sufficient that when the plunger shaft is released, the first seal is propelled by pressure differential acting across the first seal, while the distal end of the syringe is exposed to fluid, to automatically move the plunger proximally toward the end closure and cause entry of fluid into the distal portion of the bore distal of the first seal. A method of drawing fluid samples is also described.

13 Claims, 1 Drawing Sheet

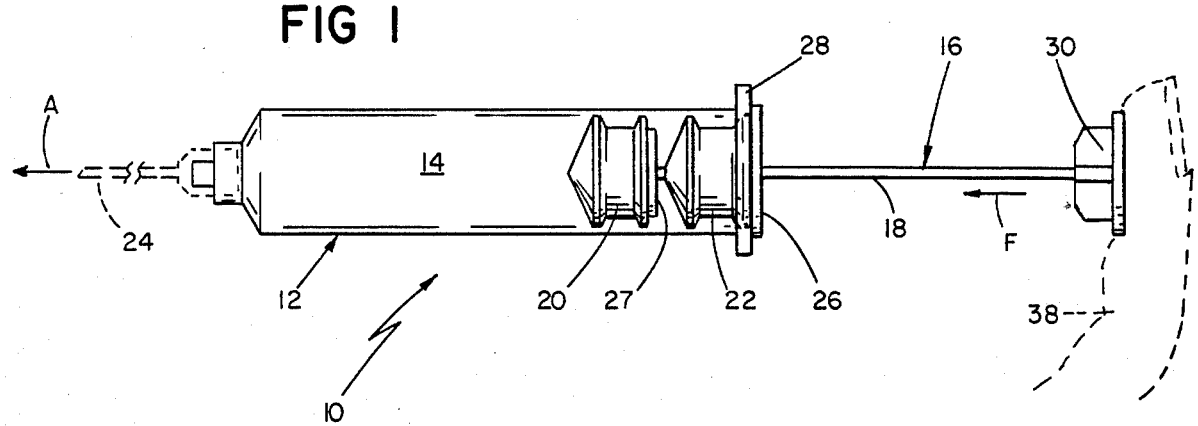
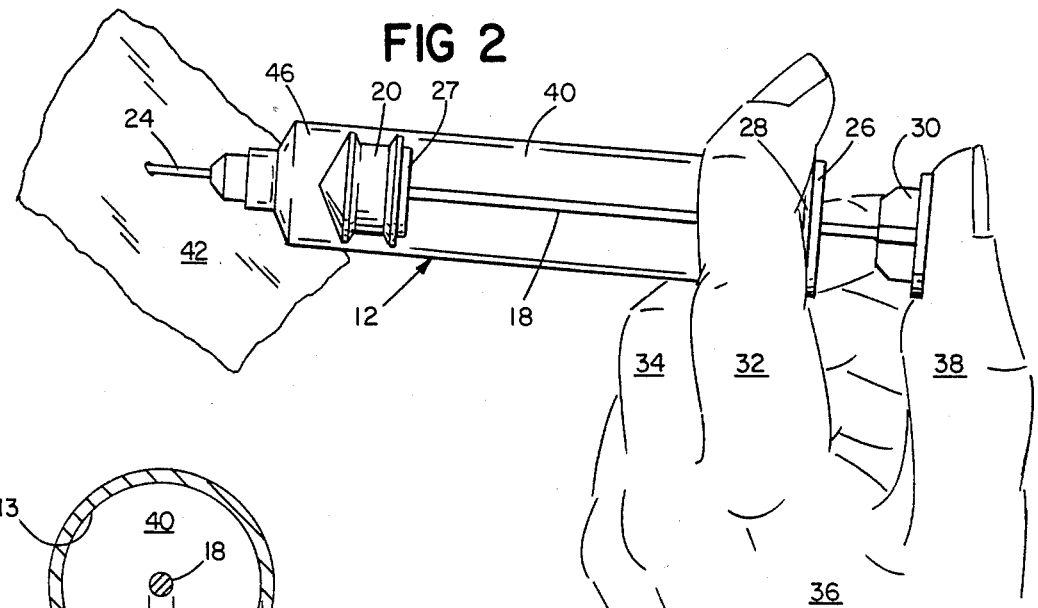
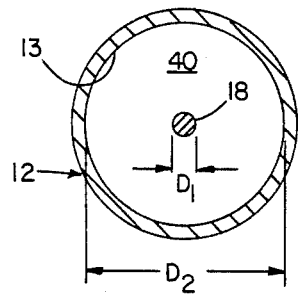
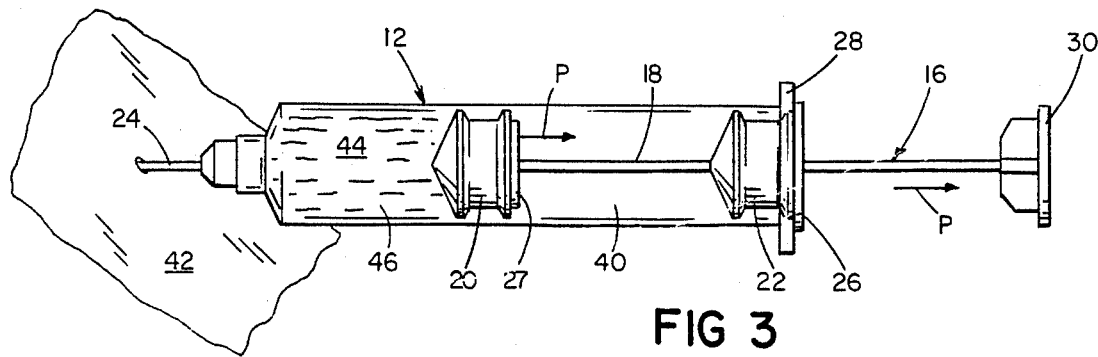

ASPIRATION SYRINGE

The invention relates to a vacuum or aspiration syringe for drawing samples, e.g., fluid or tissue, through a needle into the syringe body.

SUMMARY OF THE INVENTION

According to the invention, an aspiration syringe suitable for one-handed operation comprises a barrel defining a bore, a plunger comprising a small cross-section plunger shaft extending into the bore, and a first seal member within the bore, carried by the distal end of the shaft for axial movement within the bore, an end closure across the bore proximal of the first seal member, the plunger shaft extending in sliding, sealed engagement therethrough, the first seal member adapted to engage the wall defining the bore in vacuum-tight sealing engagement, and the transverse cross-sectional area of the shaft being of the order of much less than the transverse cross-sectional area of the bore to provide a syringe-actuating vacuum chamber of substantial volume within the bore between the seal and the closure, whereby movement of the plunger shaft to carry the first seal member distally, from a first position, away from the end closure, creates a vacuum condition within the vacuum chamber sufficient that when the plunger shaft is released, the first seal member is propelled by pressure differential acting across the first seal member, while the distal end of the syringe is exposed to fluid, to automatically move the plunger proximally toward the second seal member and cause entry of fluid into the portion of the bore distal of the first seal member.

In preferred embodiments, the transverse cross-sectional area of the shaft is less than 5%, and preferably about 2% or less, of the transverse cross-sectional area of the bore; the bore and plunger are sized to enable stroke of the plunger sufficient to create a vacuum condition of the order of 20 inches of mercury or greater within the vacuum chamber; the first seal member in the first position is disposed in close proximity to the end closure; the first seal member is adapted, upon release, to return a substantial portion of the distance toward the first position; the first seal member engages the surface defing the bore with low friction; the end closure comprises a second seal member disposed within the bore and fixed against movement relative to said barrel, preferably the first seal member and the second seal member are of double sealing ring type; and the vacuum chamber has a volume of the order of about 10 cubic centimeters, preferably the bore has a diameter of the order of about 0.5 inch, and the plunger has a maximum stroke of at least about 2 inches.

According to another aspect of the invention, a method for obtaining a fluid sample from a body by aspiration comprises the steps of: providing an aspiration syringe as described above, with the distal end of the syringe free to release air, pressing the plunger to move the first seal member away from the end closure to create a vacuum condition within the vacuum chamber, exposing the distal end of the syrirge to fluid, and releasing the plunger, the vacuum condition within the vacuum chamber being sufficient when the plunger is released to cause the plunger to automatically move proximally while drawing fluid into the bore distal of the first seal member.

In preferred embodiments, automatic movement of the plunger to draw in fluid is caused by pressure differential acting across the first seal member.

The invention thus provides an aspiration syringe that creates vacuum for drawing a sample by quick, one-handed manipulation to generate continuous vacuum while allowing the doctor to have both hands free after onset.

Other features and advantages of the invention will be understood from the following description of a preferred embodiment, and from the claims.

PREFERRED EMBODIMENT

We first briefly describe the drawings.

FIG. 1 is a side view of the aspiration syringe of the invention, as packaged prior to use;

FIG. 2 is a perspective view of the aspiration syringe of the invention, with the needle introduced through a patient's skin by a physician and the plunger depressed preparatory to taking a sample;

FIG. 3 is a side view of the aspiration syringe during sample taking; and

FIG. 4 is an end section view taken at the line 4—4 of FIG. 3.

Referring to FIG. 1, an aspiration syringe 10 of the invention consists of a syringe barrel 12 defining a bore 14, a plunger 16 consisting of a small cross-section plunger shaft 18, e.g., a hollow steel cannula, extending into the bore 14 and a first seal member 20 within the bore, and an end closure across bore 14, consisting of a second seal member 22 disposed within the bore proximal of the first seal member 20. The first seal member is carried by the distal end of the shaft 18 for axial movement within the bore. The plunger shaft extends through the second seal member 22 in sliding, sealed engagement.

The syringe barrel is a standard syringe encasement, e.g., of 10 cc volume sized and constructed at the distal end for receiving a disposable aspiration needle 24, and defining a small bore for passage of fluids between the needle and the syringe bore 14. The proximal end of the syringe barrel defines an aperture sized for receiving the first and second seal members 20, 22 into the syringe barrel, the seal members being of the double ring type and each adapted to engage the will 13 of the syringe barrel defining the bore in vacuum-tight, sealing engagement. The second, proximal seal member 22 is attached to a disk 26, sized to engage upon the end surface of the syringe barrel, about the proximal opening, to hold the second seal member fixed in position at the distal end of the syringe bore. The disk 26 also acts as a stiffener to enhance the sealing performance of seal member 22. A similar but smaller diameter disk 27 serves to enhance the sealing performance of first seal member 20. Extending radially outward about the proximal end of the syringe barrel is flange 28. The plunger shaft 18 terminates proximally in thumb tab 30.

The syringe 10 is provided generally as shown in FIG. 1, with the first distal seal member 20 disposed closely adjacent to the second, proximal seal member 22, on the plunger shaft 18, and the seals and plunger 16 inserted into the proximal end of the plunger until the disk 26 engages upon the proximal surface of syringe barrel. A disposable needle 24, shown dashed line in FIG. 1, is attached to the distal end of the syringe barrel 12.

Referring to FIG. 2, to aspirate a sample, the physician, using only one hand (36), grasps the syringe barrel 12 with adjacent fingers 32, 34 on either side of the barrel and engaging flange 28, and thumb 38 engaged upon the end surface of thumb tab 30. The physician presses thumb tab 30, e.g., with thumb 38, to move the plunger 16 in the distal direction (arrow F, FIG. 1), toward the proximal end of the syringe barrel, movement of the plunger shaft 18 carrying the first seal member 20, which engages the wall 13 defining the vacuum chamber 40 with low friction, distally from its first position (FIG. 1), away from the second seal member 22, to create a vacuum condition within a vacuum chamber 40, e.g., of about 10 cc volume, within the bore 14, between the two seal members, while expelling air (arrow A) from within the bore 14, via the needle 24.

After the thumb tab is fully depressed, a stroke, e.g., of at least about 2 inches, the physician injects needle 24 into the body 42 of the patient to a position where a fluid sample is to be taken. The relationship of the outer diameter, $D_1$, of the plunger shaft 18 to the inner diameter, $D_2$, e.g., about 0.5 inch, of the bore of the vacuum chamber 40 is selected to provide a ratio of transverse cross-sectional areas of shaft to vacuum chamber bore of the order of 1:20 or less, and preferably 1:50 or less, to provide a substantial syringe-actuating pressure differential between the vacuum chamber 40 and the sample chamber 44, across the first seal member 20. Preferably the differential is of the order of at least about 20 inches of mercury.

The physician is thus able to release the syringe, freeing both of his hands for other purposes, the vacuum condition (indicated in FIG. 3 by "—") within the chamber 40 being sufficient that when the plunger 16 is released, the first seal member 20 is propelled proximally (arrow P, FIG. 3) by pressure differential acting across the first seal member 20, to automatically withdraw the plunger proximally, toward the second seal member, returning the first seal member substantially to its first position, and causing entry of a sample 44 from body 42 into the distal sample chamber 46 of syringe bore 14. Vacuum is applied continuously, with the syringe unattended, to draw fluid sample into sample chamber 46 until the first seal member 20 returns at least substantially to its first position adjacent the second seal member 22. The needle 24 of syringe 10 is then withdrawn from the body and, when desired, the sample 44 is easily removed from the chamber 46 by again depressing thumb tab 30 (arrow F).

Other embodiments of the invention are within the following claims.

What is claimed is:

1. An aspiration syringe suitable for one-handed operation, comprising;
   a barrel defining a bore,
   a plunger comprising a small cross-section plunger shaft extending into the bore, and a first seal member within the bore, carried by the distal end of the shaft for axial movement within the bore, and
   means for generating a syringe-actuating vacuum condition, comprising: said first seal member, a stationary end closure across the bore, proximal of the first seal member, the plunger shaft extending in sliding, sealed engagement therethrough, the first seal member sized and constructed, relative to the wall defining the bore, to engage said wall in vacuum-tight sealing engagement, and the transverse cross-sectional area of the shaft being much less than the transverse cross-sectional area of the bore to provide a syringe-actuating vacuum chamber of substantial volume within the bore between said seal and said closure,
   whereby movement of the plunger shaft to carry the first seal member distally, from a first position, away from the end closure, creates a vacuum condition within said vacuum chamber sufficient that when the plunger shaft is released, the first seal member is propelled by pressure differential acting across said first seal member, while the distal end of the syringe is exposed to fluid, to automatically move the plunger proximally toward the end closure and cause entry of fluid into the portion of the bore distal of said first seal.

2. The aspiration syringe of claim 1 wherein the transverse cross-sectional area of the shaft is less than 5% of the transverse cross-sectional area of the bore.

3. The aspiration syringe of claim 2 wherein said cross-sectional area is about 2% or less than the transverse cross-sectional area of the bore.

4. The aspiration syringe of claim 1 wherein the bore and plunger are sized to enable stroke of the plunger sufficient to create a vacuum condition of the order of 20 inches of mercury or greater within said vacuum chamber.

5. The aspiration syringe of claim 1 wherein said first seal member in said first position is disposed in close proximity to said end closure.

6. The aspriation syringe of claim 1 wherein said first seal member is adapted, upon release, to return, by the force of vacuum in said vacuum chamber, a substantial portion of the distance toward said first position.

7. The aspiration syringe of claim 1 wherein said first seal member engages the surface defining said bore with low friction.

8. The aspiration syringe of any of the foregoing claims wherein said end closure comprises a second seal member disposed within said bore and fixed against movement relative to said barrel.

9. The aspiration syringe of claim 8 wherein said first seal member and said second seal member are of double sealing ring type.

10. The aspiration syringe of claim 1 wherein said vacuum chamber has a volume of the order of about 10 cubic centimeters.

11. The aspiration syringe of claim 10 wherein said bore has a diameter of the order of about 0.5 inch, and said plunger has a maximum stroke of at least about 2 inches.

12. A method for obtaining a fluid sample from a body by aspiration, said method comprising the steps of:
   providing an aspiration syringe comprising a barrel defining a bore, a plunger comprising a small cross-section plunger shaft extending into the bore, and a first seal member within the bore, carried by the distal end of shaft for axial movement within the bore, an end closure across the bore proximal of the first seal member, the plunger shaft extending in sliding, sealed engagement therethrough, the first seal member sized and constructed, relative to the wall defining the bore, to engage said wall in vacuum-tight sealing engagement, and the transverse cross-sectional area of the shaft being much less than the transverse cross-sectional area of the bore to provide a syringe-actuating vacuum chamber of substantial volume within the bore between said seal and said closure,
   with the distal end of the syringe free to release air, pressing the plunger to move the first seal member away from the end closure to create a vacuum condition within said vacuum chamber,
exposing the distal end of the syringe to fluid, and
releasing the plunger, the vacuum condition within said vacuum chamber being sufficient when said plunger is released to cause said plunger to automatically move proximally while drawing fluid into the bore distal of said first seal member.

13. The method of claim 12 wherein automatic movement of said plunger to draw in said fluid is caused by pressure differential acting across said first seal member.

* * * * *

UNITED STATES PATENT AND TRADEMARK OFFICE
CERTIFICATE OF CORRECTION

PATENT NO. : 4,766,908
DATED : August 30, 1988
INVENTOR(S) : Thomas P. Clement

It is certified that error appears in the above-identified patent and that said Letters Patent is hereby corrected as shown below:

Column 1, line 63, "syrirge" is changed to --syringe--.

Column 2, line 45, "will 13" is changed to --wall 13--.

Signed and Sealed this

Fourteenth Day of February, 1989

Attest:

DONALD J. QUIGG

*Attesting Officer*   *Commissioner of Patents and Trademarks*